United States Patent [19]
Kaplan

[11] Patent Number: 5,341,694
[45] Date of Patent: Aug. 30, 1994

[54] DIAMOND ANVIL HAVING DIAMONDS WITH CURVED EDGES

[75] Inventor: George R. Kaplan, Rye Brook, N.Y.

[73] Assignee: Lizare Kaplan International, Inc., New York, N.Y.

[21] Appl. No.: 849,867

[22] Filed: Mar. 12, 1992

[51] Int. Cl.$^5$ .................. G01N 1/28; G01N 21/84
[52] U.S. Cl. .................... 73/864.91; 425/77; 356/244
[58] Field of Search .......... 73/864.91, 860, 818; 425/77, DIG. 26; 356/36, 244, 246

[56] References Cited

U.S. PATENT DOCUMENTS

| | | | |
|---|---|---|---|
| 2,340,659 | 2/1944 | Goldstein | 63/32 |
| 2,554,901 | 5/1951 | Fromholt | 73/85 |
| 3,141,746 | 7/1964 | De Lai | 425/DIG. 26 X |
| 3,169,273 | 2/1965 | Brayman | 425/77 |
| 3,227,068 | 1/1966 | Newhall | 425/DIG. 26 UX |
| 4,776,223 | 10/1988 | Moss | 73/864.91 |
| 5,200,609 | 4/1993 | Sting et al. | 356/244 X |

FOREIGN PATENT DOCUMENTS

| | | | |
|---|---|---|---|
| 458672 | 11/1991 | European Pat. Off. | 356/244 |
| 10724 | 3/1971 | Japan | 425/77 |
| 365276 | 3/1973 | U.S.S.R. | 425/77 |
| 573182 | 9/1977 | U.S.S.R. | 356/244 |
| 1410492 | 10/1975 | United Kingdom | 356/244 |

OTHER PUBLICATIONS

"Phonograph Styli"; *Consumer Reports*; Aug. 1954 pp. 364–365.

*Primary Examiner*—Tom Noland
*Attorney, Agent, or Firm*—Sprung Horn Kramer & Woods

[57] ABSTRACT

A diamond anvil of the type comprising (a) a pair of diamonds having a facing, plane parallel bearing surfaces and (b) a device for applying a force to the diamonds tending to press the bearing surfaces together. Both diamonds have a peripheral surface, extending outward from the bearing surface, which is tangent to the bearing surface at the interface thereto and which tapers away from the bearing surface with a continuous curved surface.

6 Claims, 3 Drawing Sheets

DIAMOND ANVIL HAVING DIAMONDS WITH CURVED EDGES

BACKGROUND OF THE INVENTION

The present invention relates to the structure of diamonds which are used in a so-called "diamond anvil".

A diamond anvil is an apparatus which allows direct viewing or monitoring of a material that is highly compressed between two surfaces. *Scientific American,* Vol. 250 (April, 1984) pp. 54–62. Diamond anvil apparatus includes a pair of circularly shaped diamonds coaxially arranged with facing, plane parallel bearing surfaces and a device for applying a force to these diamonds tending to press the bearing surfaces together. Pressures higher than those at the center of the earth have been achieved with this apparatus.

The diamond anvil has been developed from the so-called "Bridgeman anvil", circa 1905, which used tungsten carbide for one or both of the pressure producing surfaces and was opaque to visible wavelength radiation. In 1959, Weir, Lippincott, Van Valkenberg and Bunting, of the National Bureau of Standards and, independently, Jamieson, Lawson and Nachtrieb of the University of Chicago, fabricated the first diamond anvils for high pressure materials investigation. Conventionally, diamond anvil apparatus has employed circularly shaped, brilliant cut diamonds arranged coaxially with their top or bottom facets facing each other and serving as the bearing surfaces that apply a force to the test material. This force tending to press the bearing surfaces together which may be generated by a hydraulic press or a screw device, etc., is applied in the axial direction to the opposite facing surfaces of the two diamonds.

In order to prevent the test material from being squeezed out of the space between bearing surfaces, a malleable gasket is arranged between the two diamonds. This gasket has a central opening for the test material and comes in contact with the edges of the bearing surfaces on opposite sides. When the bearing surfaces of the two diamonds are pressed toward each other, the gasket is compressed permitting the diamonds to approach each other and apply a force to the test material.

Due to enormous and often unequal forces generated during a test, the sharp edges of the bearing surfaces tend to fracture or crack. Such fractures, when they occur, prevent the even application of force to the test material.

Efforts have been made to reduce the fragility of the diamond edges by providing one or more rows of bevels adjacent to the bearing surface edges so that included angles are not as sharp. See U.S. Pat. No. 4,776,223. However, even this configuration has angular edges which are relatively fragile.

SUMMARY OF THE INVENTION

It is therefore a principal object of the present invention to provide diamond anvil apparatus which is not subject to the diamond fractures that occur at the fragile edges of the bearing surfaces.

This object, as well as other objects which will become apparent from the discussion that follows, are achieved, according to the present invention, by providing both diamonds with a peripheral surface, extending outward from the bearing surface, which is tangent to the bearing surface at the interface thereto and which tapers away from the bearing surface with a continuous curved surface.

It has been discovered that the fractures at the fragile edges of the bearing surfaces can be prevented by substituting curved surfaces, which blend into the flat bearing surfaces, for the sharp edges at the peripheries of the bearing surfaces.

The peripheral surfaces have a constant radius of curvature or any similar curvature which maximally resists fracture.

The preferred embodiments of the present invention will now be described with reference to the accompanying drawings.

DESCRIPTION OF THE PREFERRED EMBODIMENTS

Figure 1:
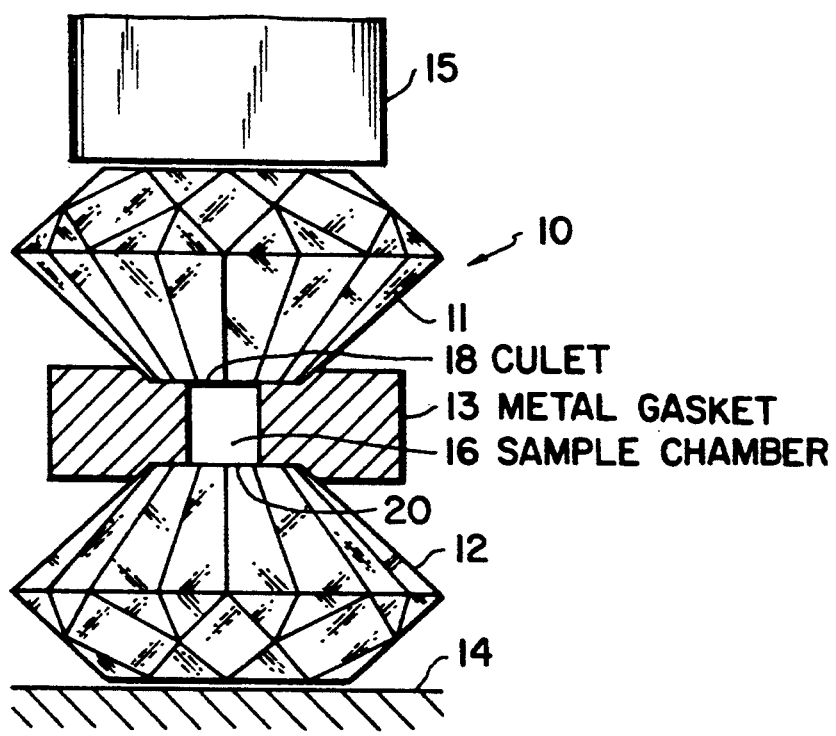
FIG. 1 is an elevational view, partly in cross section, showing the principal components of diamond anvil apparatus as it is known in the prior art.

FIG. 1 illustrates typical diamond anvil apparatus as it is known in the art. The apparatus 10 comprises a circularly shaped upper diamond 11, a circularly shaped lower diamond 12, and a metal gasket 13 arranged coaxially between a base 14 and a hydraulic press 15 for applying a compressive force to the two diamonds and the metal gasket.

The metal gasket is provided with a sample chamber 16 for the material to be tested between the facing, plane parallel bearing surfaces 18 and 20 of the upper diamond and lower diamond, respectively.

Figure 2:
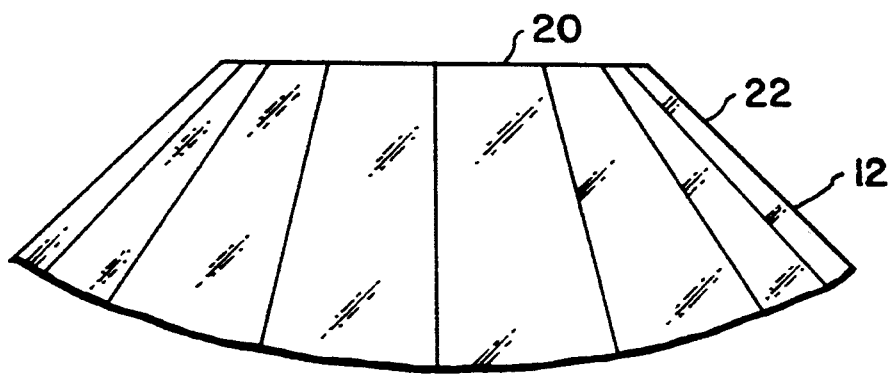
FIG. 2 is an enlarged, detailed elevational view of the bearing surface of a diamond employed in the diamond anvil apparatus of FIG. 1.

As is shown in greater detail in FIG. 2, the bearing surface 20 has a sharp edge at its periphery which merges into the tapered facets 22 of the diamond. This sharp edge is subject to fracture when urged, with great compressive force, against the facing diamond.

Figure 3:
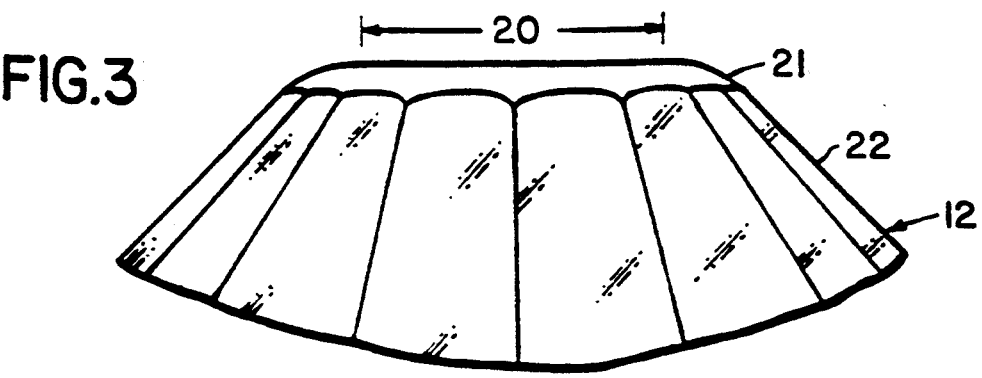
FIG. 3 is an enlarged, detailed elevational view of the bearing surface of a diamond for use in the diamond anvil apparatus of FIG. 1, according to a preferred embodiment of the present invention.
Figure 4:
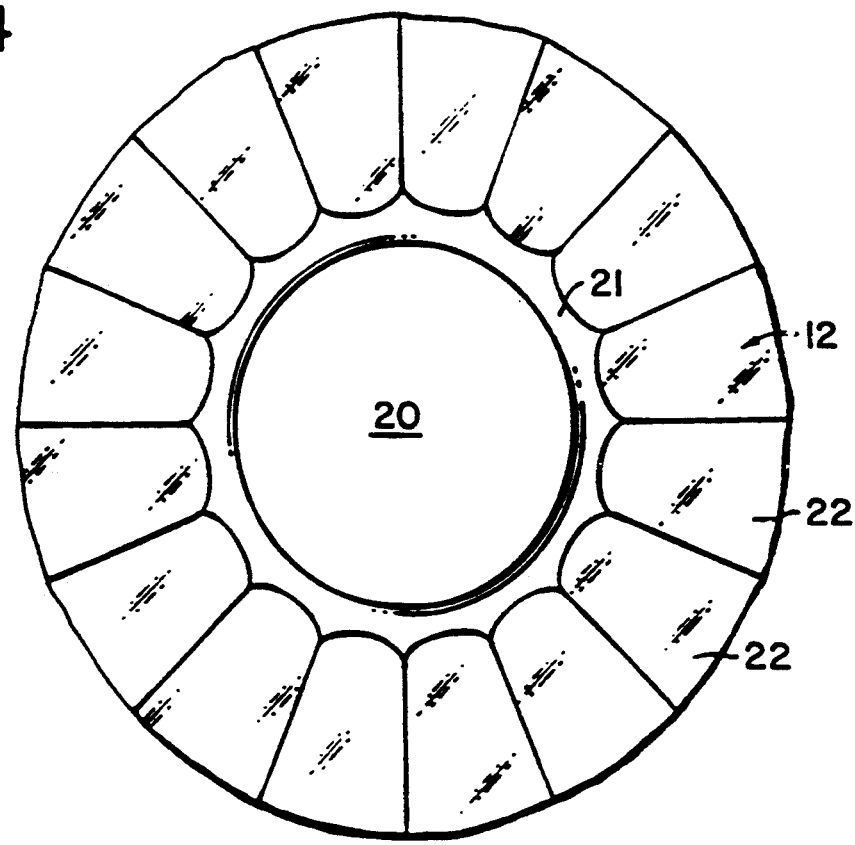
FIG. 4 is a plan view of the diamond bearing surface of FIG. 3.
Figure 5A:
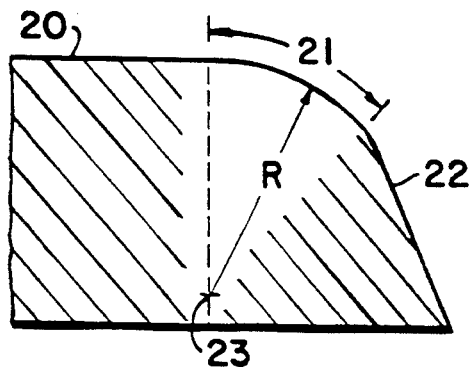
FIGS. 5A and 5B are cross-sectional views of one edge of the diamond bearing surface of FIG. 3 showing the curvature in detail.
Figure 5B:
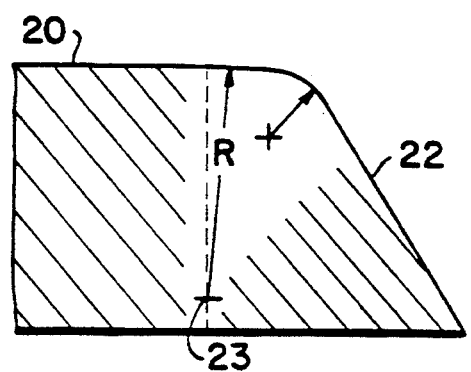

FIGS. 3 and 4 illustrate the improvement according the present invention wherein the sharp edges at the periphery of the bearing surface are replaced by a curved peripheral surface that blends into the planar bearing surface and eliminates the fragile area. As is shown in further detail in cross-section in FIG. 5A, the curved surface 21 may have a constant radius R which originates from a point on a line 23 extending axially through the diamond and terminating at the edge of the bearing surface 20. Alternatively, as shown in FIG. 5B, the radius of curvature may change continuously from a value R on line 23 to a greater or lesser value to form a parabola or some other smooth curve. In any case, the curved surface 21 is made tangent to the bearing surface 20 at the periphery thereof; i.e, where the line 23 (or, more correctly, the cylinder) intersects.

The curved surface 21 can be formed by any known method or means. For example, these surfaces may be formed by the well-known technique of producing hemispherical surfaces on diamond phonograph needles.

Figure 6:
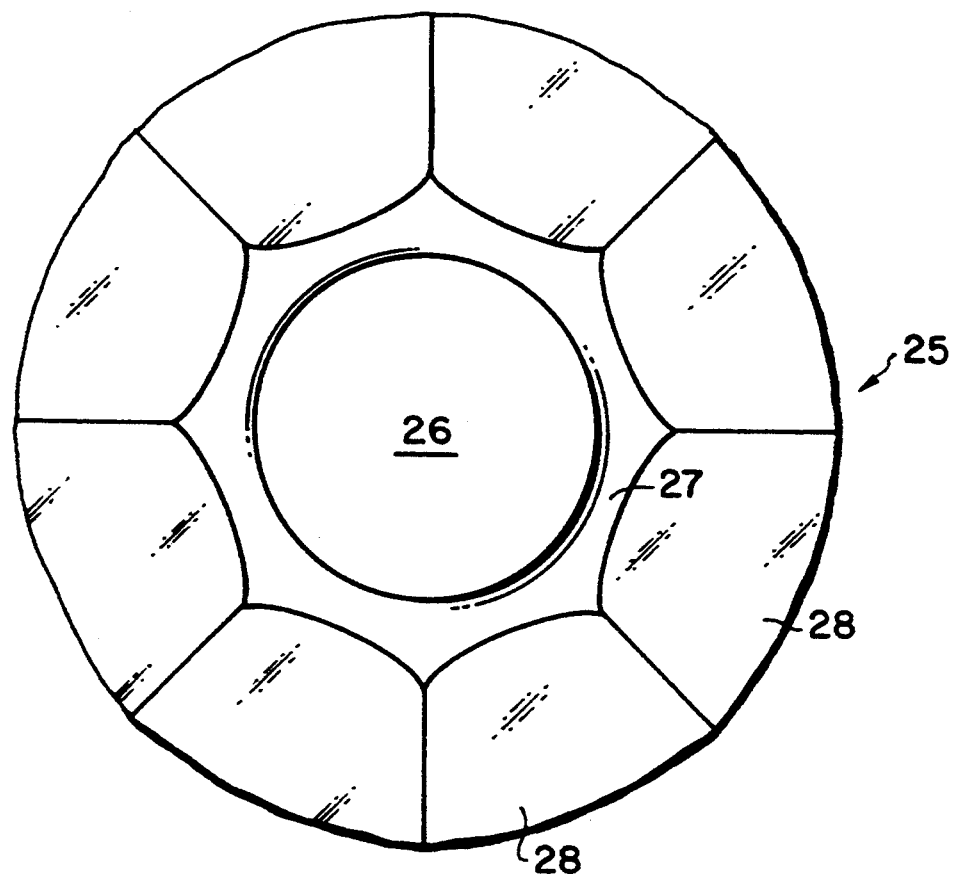
FIG. 6 is a plan view the bearing surface of a diamond with fewer facets than the diamond of FIGS. 3 and 4, such bearing surface having a curved peripheral surface according to the present invention.
Figure 7:
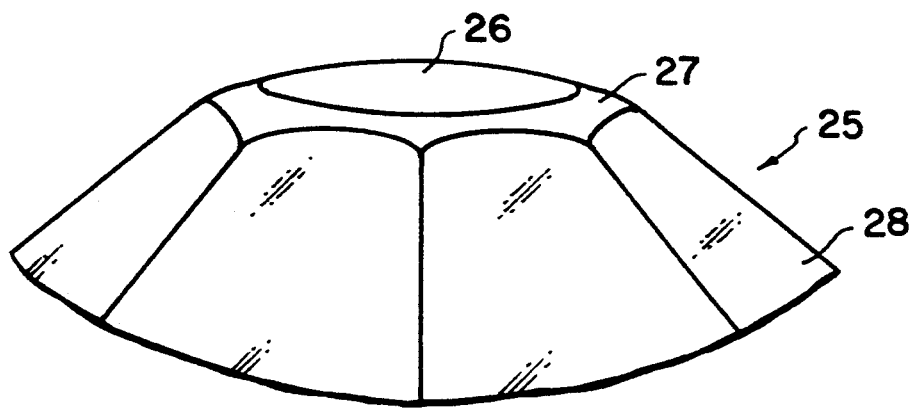
FIG. 7 is a perspective view of the diamond bearing surface of FIG. 6.

By reducing the danger of fracture, the present invention makes it possible to increase the pressure achievable before the diamond anvils fail. FIGS. 6 and 7 illustrate the application of the invention to a diamond having eight facets around its periphery. Provision of a continuous curved surface 27 at the periphery of the bearing surface 26 in a diamond 25 eliminates the sharp edges which would otherwise be present.

There has thus been shown and described a novel diamond anvil which fulfills all the objects and advantages sought therefor. Many changes, modifications, variations and other uses and applications of the subject invention will, however, become apparent to those skilled in the art after considering this specification and the accompanying drawings which disclose the preferred embodiments thereof. All such changes, modifications, variations and other uses and applications which do not depart from the spirit and scope of the invention are deemed to be covered by the invention, which is to be limited only by the claims which follow.

What is claimed is:

1. In diamond anvil apparatus comprising (a) a pair of diamonds having facing, plane parallel bearing surfaces and (b) means for applying a force to said diamonds tending to press said bearing surfaces together, the improvement wherein both of said diamonds have a peripheral surface, extending outward from said bearing surface, which is tangent to said bearing surface at the interface thereto and which tapers away from said bearing surface with a continuous curved surface.

2. The apparatus defined in claim 1, wherein said continuous curved surface has a constant radius of curvature.

3. The apparatus defined in claim 1, wherein said continuous curved surface has a continuously changing radius of curvature.

4. A diamond for use in diamond anvil apparatus that comprises (a) a pair of diamonds having a facing, plane parallel bearing surfaces and (b) means for applying a force to said diamonds tending to press said bearing surfaces together, said diamond having a peripheral surface, extending outward from said bearing surface, which is tangent to said bearing surface at the interface thereto and which tapers away from said bearing surface with a continuous curved surface.

5. The diamond defined in claim 4, wherein said continuous curved surface has a constant radius of curvature.

6. The diamond defined in claim 4, wherein said continuous curved surface has a continuously changing radius of curvature.

* * * * *